(12) United States Patent
Steiger et al.

(10) Patent No.: US 6,616,667 B1
(45) Date of Patent: Sep. 9, 2003

(54) SURGICAL INSTRUMENT FOR TENSIONING A CABLE-LIKE TENSIONING ELEMENT

(75) Inventors: Marco Steiger, Arnegg (CH); Hermann Breimesser, Elgg (CH); Simon Casutt, Gossau (CH); Reto Braunschweiler, Neftenbach (CH)

(73) Assignee: Sulzer Orthopedics, Ltd., Baar (CH)

( * ) Notice: Subject to any disclaimer, the term of this patent is extended or adjusted under 35 U.S.C. 154(b) by 0 days.

(21) Appl. No.: 09/718,163

(22) Filed: Nov. 21, 2000

(30) Foreign Application Priority Data

Nov. 25, 1999 (EP) .............................. 99811087
Dec. 22, 1999 (EP) .............................. 99811194

(51) Int. Cl.⁷ .............................. A61B 17/56
(52) U.S. Cl. .............................. 606/61; 606/103
(58) Field of Search .............................. 606/53, 60, 61, 606/72, 74, 86, 102, 103, 104, 98, 57; 254/134.6, 234, 243, 244, 248; 294/81.1, 135

(56) References Cited

U.S. PATENT DOCUMENTS

| 4,050,464 A | * | 9/1977 | Hall .............................. 128/303 R |
| 5,628,751 A | * | 5/1997 | Sanders et al. .............................. 606/104 |
| 5,782,831 A | | 7/1998 | Sherman et al. |
| 6,368,326 B1 | * | 4/2002 | Dakin et al. .............................. 606/103 |

FOREIGN PATENT DOCUMENTS

| CH | 303821 | 12/1954 |
| CH | 303821 | 2/1955 |
| EP | 0625336 A2 | 11/1994 |
| EP | 0625336 A2 | 11/1994 |
| FR | 277449 A1 | 10/1999 |
| FR | 2777449 | 10/1999 |

* cited by examiner

Primary Examiner—Linda C. M. Dvorak
Assistant Examiner—Aaron Roane
(74) Attorney, Agent, or Firm—Townsend and Townsend and Crew, LLP

(57) ABSTRACT

The surgical instrument for tensioning a cable-like, a band-like or a cord-like tensioning element (5) comprises a manually actuatable lever system. Two levers (1, 2)—the first and the second actuation lever—are jointedly connected by a third lever (3). In a basic position of the system the tensioning element can be laid into a laying-in opening (15) of the first lever and into a clamping gap (32) at the second and at the third lever. One of the actuation levers (2) is formed in one section as a beam (20', 21') which is elastic in bending. The extent of a shape change of the beam can be measured. A relationship between this shape change and a tension in the tensioning element is known. The tension can be set as a result of this knowledge and of a measurement (209, 211; 8) of the shape change, or a means a tension monitor or sensor, serving for the same purpose is provided for determining a torque which acts at the corresponding actuation lever (2).

11 Claims, 4 Drawing Sheets

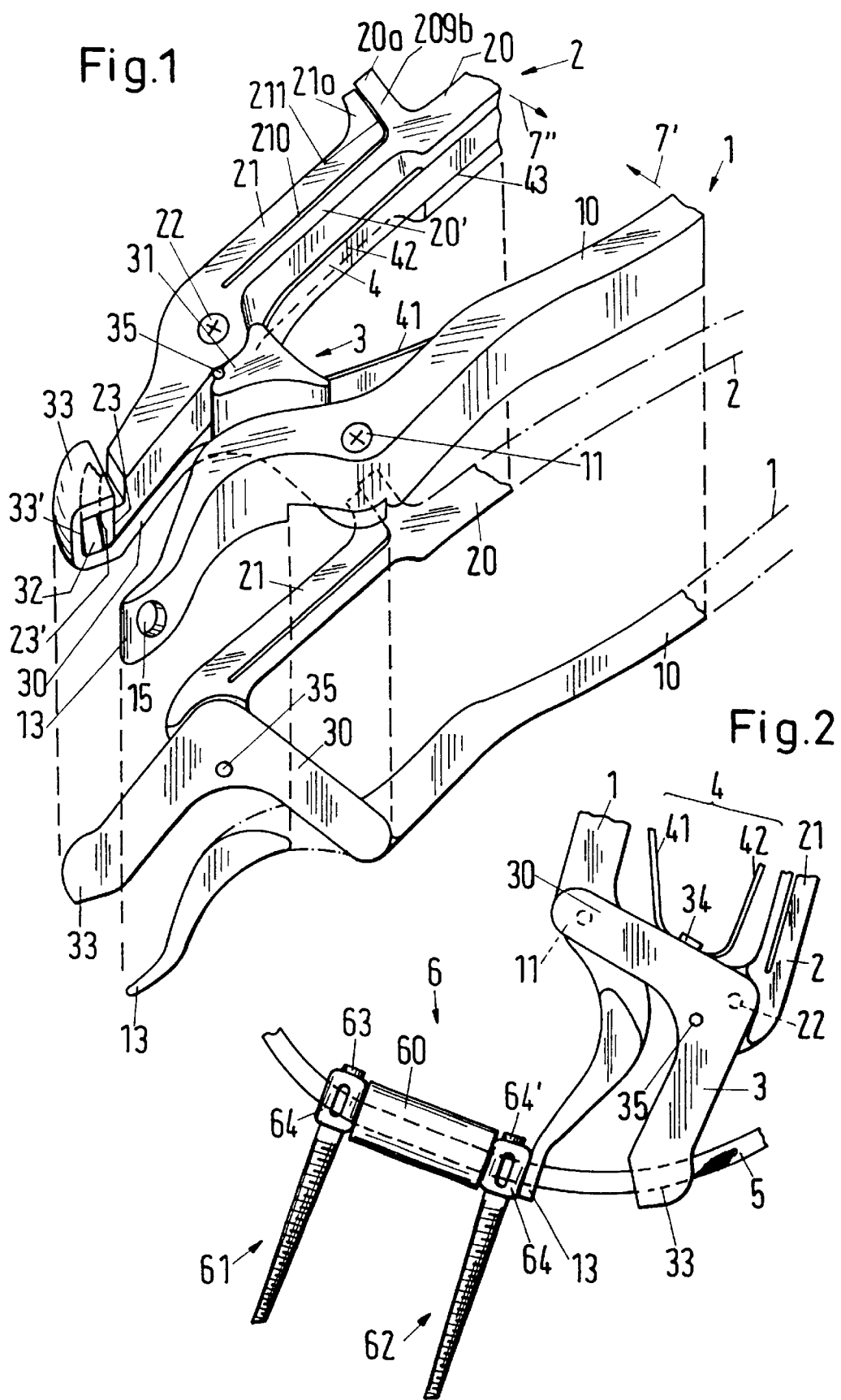

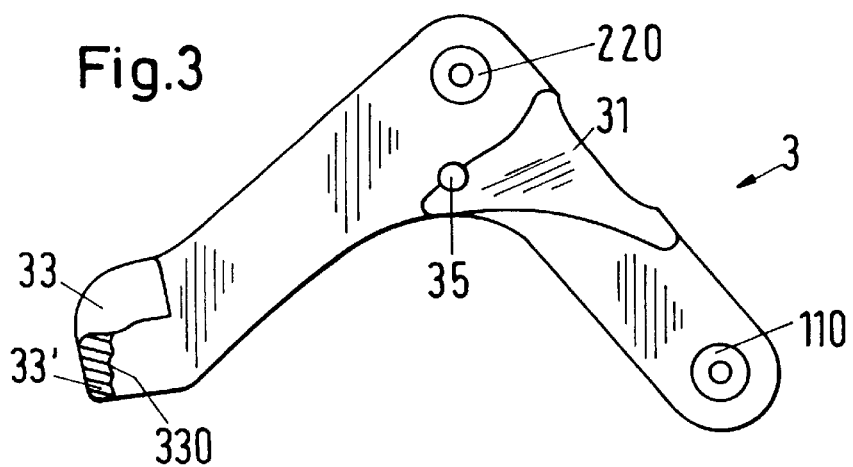
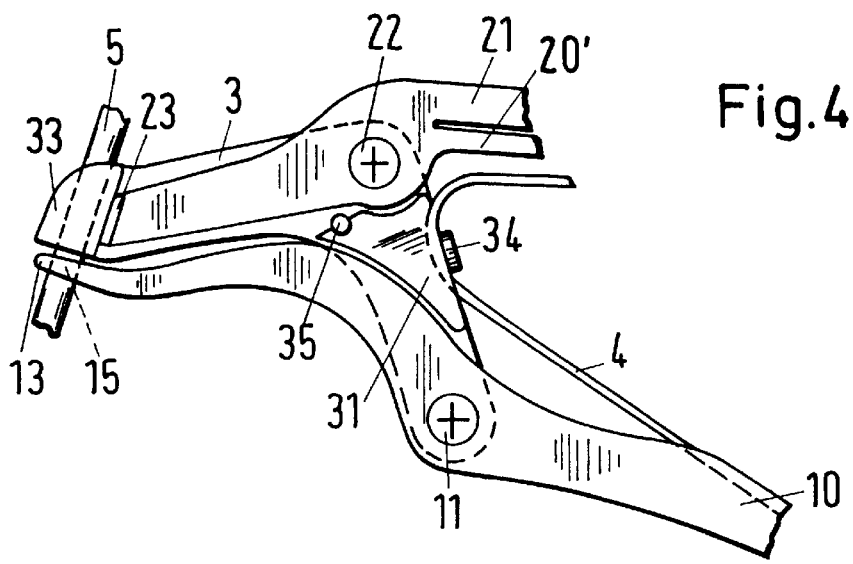
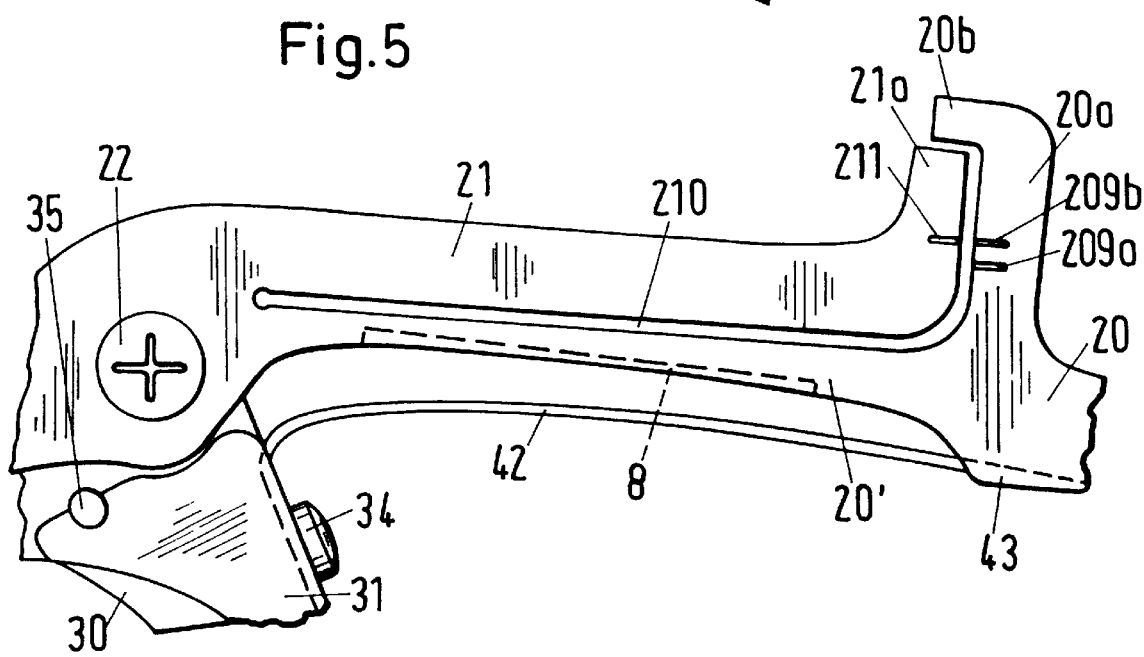

SURGICAL INSTRUMENT FOR TENSIONING A CABLE-LIKE TENSIONING ELEMENT

BACKGROUND OF THE INVENTION

The invention relates to a surgical instrument for tensioning a cable-like, a band-like or a cord-like tensioning element.

The tensioning element can for example be a cable formed of metal wires, a thread compound formed of plastic filaments or a linear mesh-work of yarns. A tensioning element of this kind will also be designated as a band for short.

Dwyer developed an operating technique for the surgical treatment of curvatures of the spine (scoliosis) in which a series of adjacent vertebrae are tensioned together by means of cables and screws within the body of a patient to form a stiffened part of the spine. A cable tensioning device is used in this operation. A device of this kind is known from GB-A-1 551 707. This cable tensioning device comprises a first lever-like part and a second part which is formed as a gripper element for the cable. These two parts are connected to one another via a main joint. The second part is a lever system in which levers are connected to one another via three joints. Two of these levers form a clamping gap of the gripper element.

An alternative surgical instrument for tensioning bands was developed which is assembled from fewer mutually movable individual parts in comparison with the above-named cable tensioning device and which can be characterized as a manually actuatable lever system with the following features:

The lever system consists of two actuation levers which are jointedly connected by a third lever, and springs which are arranged between the levers. In this a stable basic position of the system is given by the springs, which are under mechanical stress, and by movement limitations which act between the actuation levers and the third lever. A laying-in opening for the tensioning element is arranged at a tip of the first actuation lever, and a first jaw to a clamping gap for the tensioning element is arranged at a tip of the second actuation lever. A second jaw to this clamping gap is located at the third lever. In the basic position of the system the tensioning element can be inserted into the laying-in opening of the first actuation lever and into the clamping gap at the second actuation lever. Through a manual pressing together of the actuation lever, the second actuation lever makes a pivotal movement with respect to the third lever as a result of which the clamping gap is narrowed, so that the tensioning element is clamped firmly. Through a further pressing together the distance between the tips of the two actuation levers increases. The third lever is formed symmetrically as a bow with two side plates, with the actuation levers being pivotally arranged between the side plates at journaling bolts and with the journaling bolts being secured in bores of the two side plates. The clamping jaw of the third lever is located at the crown position of the bow. Together with the other clamping jaw and parts of the side plates, a laterally closed passage for the band is given. In this system consisting of three levers, the manufacture of the joint bearings proved to be complicated and expensive.

SUMMARY OF THE INVENTION

It is an object of the invention to create an instrument which can be used as a band tensioning device and which is formed as a three lever system in such a manner that the tension acting on the band during the tensioning can be determined. In addition a form of this instrument should be provided for which the instrument can be assembled without problem from the three levers.

The surgical instrument for tensioning a cable-like, a band-like or a cord-like tensioning element comprises a manually actuatable lever system. Two levers—the first and the second actuation lever—are jointedly connected by a third lever. In a basic position of the system the tensioning element can be laid into a laying-in opening of the first lever and into a clamping gap at the second and at the third lever. One of the actuation levers is formed in one section as a beam which is elastic in bending. The extent of a shape change of the beam can be measured. A relationship between this shape change and a tension in the tensioning element is known. The tension can be set as a result of this knowledge and of a measurement of the shape change, or a means serving for the same purpose is provided for determining a torque which acts at the corresponding actuation lever. The basic position is preferably a stable position, namely as a result of at least one spring which is arranged between the levers or as a result of another means which exerts corresponding forces.

The third lever is formed asymmetrically and has only one side plate. Journalling bolts for two lever joints are parts of the third lever. A single spring is secured at the third lever. A clamping jaw of the third lever is the base surface of a U-shaped passage. The spring has two limbs which in each case lie in contact at the inner flanks of the actuation lever under a mechanical stress. One clamping jaw of the second lever dips into the U-shaped passage. A movement limitation which acts between the second and the third lever is given by a separately insertable abutment pin.

BRIEF DESCRIPTION OF THE DRAWINGS

FIG. 1 shows an instrument in accordance with the invention,

FIG. 2 shows the front part of this instrument with a band which is placed under a tension, FIG. 3 shows a third lever of the instrument in accordance with the invention, FIG. 4 shows the front part of the instrument with firmly clamped band, FIGS. 5–7 show in each case cut-outs of a second actuation lever with means for carrying out a force measurement.

DESCRIPTION OF THE PREFERRED EMBODIMENTS

Figure 6:
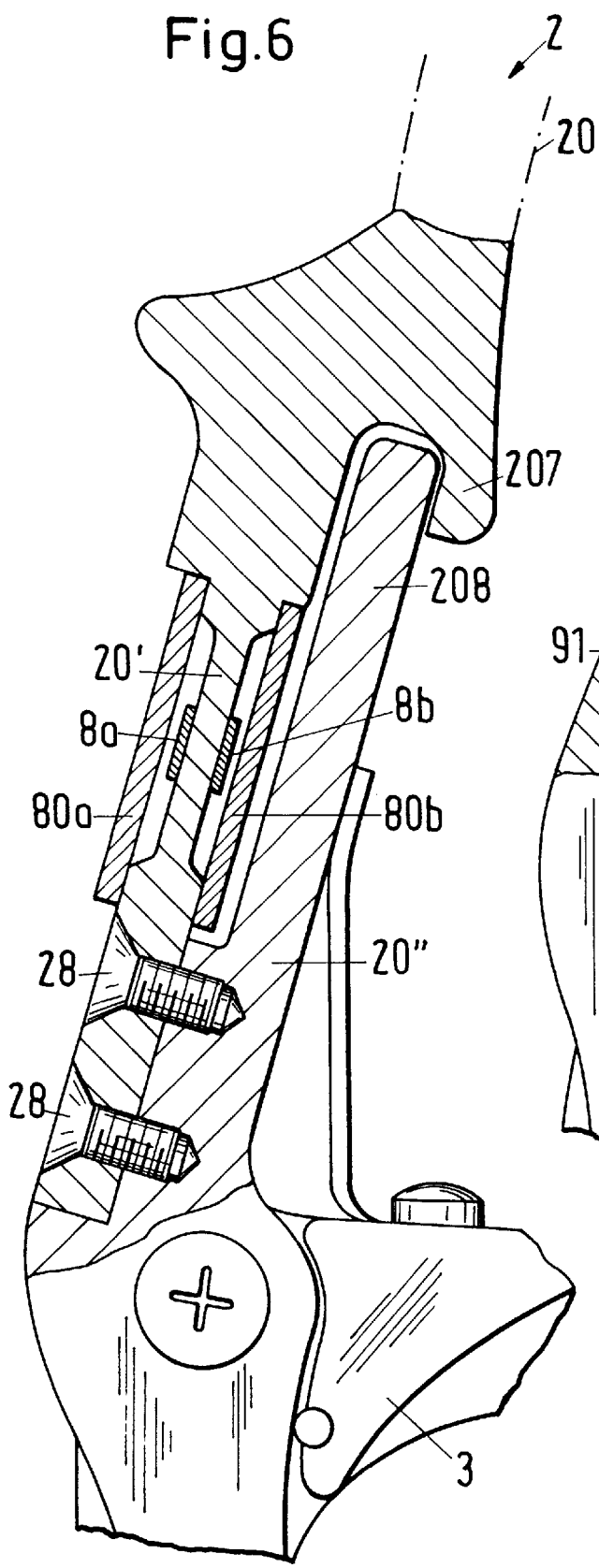

The instrument in accordance with the invention which is shown in FIG. 1, the band tensioning device, comprises a lever system which consists of two levers 1 and 2 which are connected by a third lever 3 at joints 11 and 22. The first two levers 1, 2, namely the first and the second actuation lever, have hand grips 10 and 20 which are only partly illustrated in FIG. 1. The instrument is asymmetrically designed; the visible side differs from the not visible side, which is illustrated as a mirror image in the lower half of FIG. 1 (with only the surfaces of the lowermost side plane being illustrated and with the hand grips 10 and 20 being partly indicated in chain-dotted lines).

Through a spring 4—which is arranged between the levers 1, 2 and 3, and which is under a mechanical stress—and movement limitations a stable basic position of the system is given. A movement limitation between the first actuation lever 1 and the third lever 3 is formed by a part 31 of the third lever 3. A movement limitation between the second actuation lever 2 and the third lever 3 is formed by an abutment pin 35. In FIG. 1 an imaginary lever position can be seen which illustrates the first actuation lever 1 in a deflected-out position and the other two levers 2 and 3 in the positions which they have in the basic position.

A laying-in opening 15 for a cable-like, a band-like or a cord-like tensioning element or band 5 for short—see FIG. 2—is arranged at a tip 13 of the first actuation lever 1. A first jaw 33' to a clamping gap 32 for the band 5 is arranged at a tip 33 of the third lever 3. A second jaw 23' to this clamping gap 32 is located at one end 23 of the second actuation lever 2. In the basic position of the system the band 5 can be inserted into the laying-in opening 15 of the first actuation lever 1 and into the clamping gap 32 at the second actuation lever 2. Through a manual pressing together of the actuation levers 1 and 2—indicated by arrows 7' and 7"—the second actuation lever 2 executes a small pivotal movement relative to the third lever 3, as a result of which the clamping gap 32 narrows, so that the band 5 is clamped firmly. Through a further pressing together a spreading movement results, through which the distance between the tips 13 and 33 of the two actuation levers 1 and 2 increases.

FIG. 2 shows the front part of the instrument in accordance with the invention, by means of which the band 5 has been placed under a tension through the named spreading movement. In this the band 5 is fixed with a cylindrical screw 63 in the head 64 of a first pedicular screw 61. The band 5, which passes from the first pedicular screw 61 through a plastic tube 60 (so-called cushion) to the head 64' of a second pedicular screw 62, can be fixed there in the tensioned state by means of a further cylindrical screw 63'. The unit 6 which is formed by the pedicular screws 61, 62 and the tube 60 is used in a spinal cord operation to fix two adjacent vertebrae at a distance which is given by the length of the tube 60.

The third lever 3—see FIG. 3—is designed asymmetrically with only one side plate 30. Journalling bolts 110, 220 for the two lever joints 11, 22 are parts of the third lever 3. The actuation levers 1 and 2, which have bores corresponding to the bolts, are attached to the bolts 110, 220, with rotatable connections being produced with screws.

The clamping jaw 33' of the third lever 3 forms the base surface of a U-shaped passage. The clamping jaw 23' of the second lever 2 dips into the U-shaped passage. The movement limitation which acts between the second actuation lever 2 and the third lever 3 is given by a separately insertable abutment pin 35. For geometrical reasons the actuation lever 2 can be combined only with the third lever 3 when the abutment pin 35 is still absent.

The spring 4 is secured to the third lever 3 with a screw 34—see FIG. 2. It has two limbs 41 and 42, which in each case lie in contact at inner flanks 43 of the actuation levers 1 and 2 under a mechanical stress, with it being possible for the limbs 41 and 42 to slide in grooves of the inner flanks 43. The laying-in opening 15 of the first actuation lever 1 is an eye; it can however also be designed in the manner of a fork as a gap between two prongs. The jaws 23' and 33' of the clamping gap 32 advantageously have ribbings on clamping surfaces 230, 330, with ribbing edges preferably being oriented transversely to the direction of the tension acting on the band 5.

FIG. 4 shows the front part of the instrument with a firmly clamped band 5. The actuation lever 1 is still in the basic position. The abutment pin 35 has a spacing from the actuation lever 2.

The actuation lever 2 is formed on the side of the hand grip 20 along a section as a beam 20' which is elastic in bending—see FIGS. 1 and 5. The extent of a shape change of the beam 20' can be measured. A relationship between this shape change and a tension in the band 5 can be determined and is assumed to be known. In the actuation of the band tensioning device the tension in the band 5 can be controlled and thus set as a result of this knowledge and of a measurement of the shape change. The beam 20' which is elastic in bending is arranged adjacently to a reference beam 21. The two beams 20' and 21 extend parallel to one another along a gap 210. Segments 20a and 21a are connected to the beams 20' and 21 transversely to the gap 210. Markings 209a, 209b, 211 are applied to the segments 20a and 21a respectively for determining the shape change. The marking lines 209b and 211 are for example applied in such a manner that the latter come to lie on a common straight line—cf. FIG. 5—when a tension in the band 5 is reached which should not be exceeded. The marking line 209a can specify a zero point for which the band 5 is already fixed in the clamping gap 32 without a tension already acting in this situation. It can be provided to apply the markings to separately mountable lamina. These lamina can be mounted in accordance with a zero point which is empirically determined.

The segment 20a at the beam 20' which is elastic in bending can be formed geometrically in such a manner that a bending limitation results in a cooperation with the segment 21a at the reference beam 21. An example of a bending limitation of this kind is illustrated in FIG. 5; the end 20b of the segment 20a is designed to be hook shaped.

A sensor, in particular a strain gauge 8, can be attached to the beam 20' which is elastic in bending. The sensor is part of an electrical and/or electronic measurement device (not illustrated) for displaying the tension acting in the band 5. The measurement device can be integrated at or into the actuation lever on which the sensor is arranged.

FIG. 6 shows a second example with a strain gauge. The actuation lever 2 is assembled from a hand grip part 20 and a front part 20" with two screws 28. Two strain gauges 8a, 8b are attached at two flanks of a beam 20' which is elastic in bending. Two soft cover layers 80a, 80b, the influence of which on the shape change of the beam 20' is practically negligible, serve for the encapsulation of these sensors. A cam 207 and a beam 208 act as a bending limitation for the purpose of an overload protection.

Figure 7:
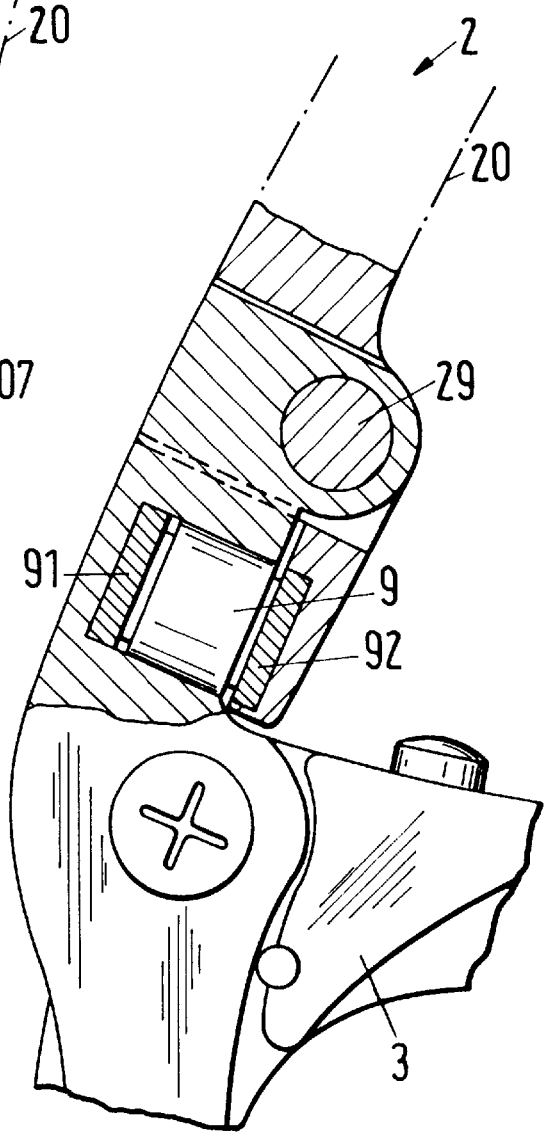

A further possibility for monitoring the tension in the band 5 is illustrated in FIG. 7, namely a means for determining the torque which acts at the actuation lever 2 during the tensioning of the band 5. This lever 2 is likewise assembled from a hand grip part 20 and a front part 20'", but here via a joint 29. A piezoelectric crystal 9, which is arranged between two hardened platelets 91 and 92 of the two parts 20" and 20 respectively, is placed under a pressure during the pressing together of the two actuation levers 10 and 20 which is proportional to the torque acting at the lever 2 and is thus also proportional to the tension of the band 5.

Pertaining to measurement chains between the sensors and display devices the following remarks can be added: A signal evaluation takes place in the display device. The display of the result of this signal evaluation takes place optically and/or acoustically. If the sensor is a strain gauge, then a current supply is necessary. If the sensor is a piezoelectric crystal, then the possibility of a zero compensation is necessary. A measurement value amplifier for a voltage or current signal (strain gauge) or for a charge amplification (piezoelectric crystal) respectively can be integrated into the instrument or into the display device. The strain gauges can be connected together in a half or a full bridge circuit. A cable for the connection between the measurement value amplifier and the display device must be capable of water vapor sterilization and have a kink protection. Preferred materials for the insulation material are silicone rubber and/or Teflon. Interfaces between the instrument and the cable, and between the cable and the display device, must be suitable for medical uses, i.e. be present in the form of plug connections which can be sterilized and hermetically sealed off. The interface between the instrument and the cable can be fixed instead of releasable.

Figure 8:
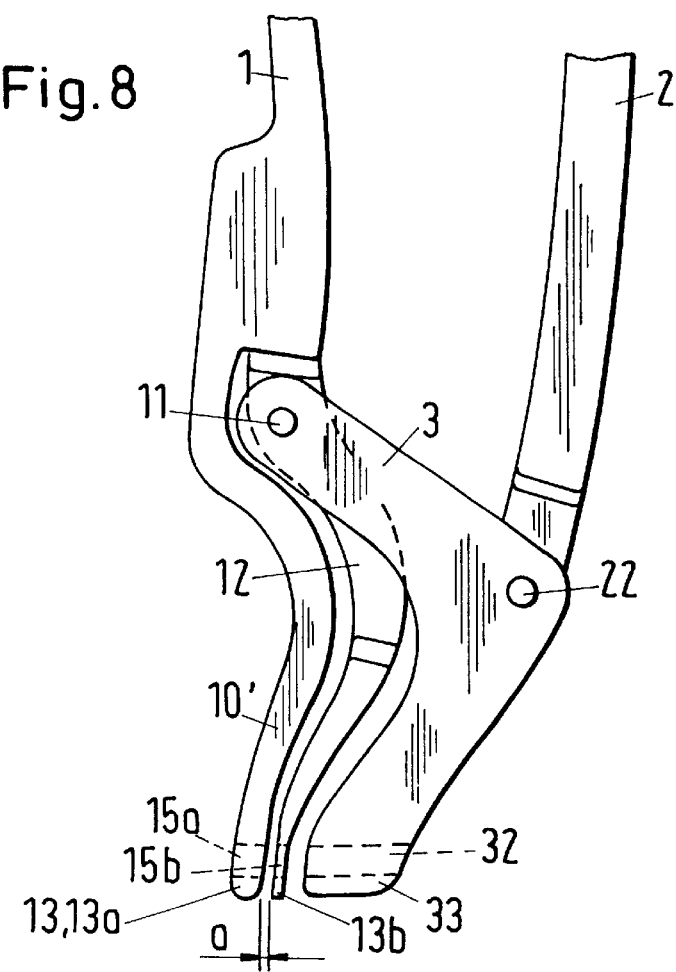
FIG. 8 shows an alternative to the mechanical exemplary embodiment of FIGS. 1 to 5.

An alternative to the mechanical exemplary embodiment of FIGS. 1 to 5, i.e. to the example of the band tensioning device in accordance with the invention, in which the tension in the band 5 to be tensioned is monitored with a mechanical display, is shown in FIG. 8. In this example a section which is designed as a beam 10' which is elastic in bending is a part of the first actuation lever 1, and indeed a part in the sigmoidally shaped front region between the tip 13 and the joint 11. A reference beam 12 is a second part of the front region. The joint 11 which produces the connection between the actuation lever 1 and the third lever 3 is located at the base of this reference beam 12. During the tensioning of a non-illustrated band 5 (cf. FIG. 2) a distance a between the beams 10' and 12 at their tips 13a and 13b respectively decreases (proportionally to the tension). A distance "a" which is given in the basic position is advantageously made so great that the beams 10' and 12 make contact when a desired tension is reached, i.e. the distance a becomes zero. Both beams 10' and 12 contain at their tips 13a, 13b laying-in openings 15a and 15b respectively for the band 5. Since the surgeon can recognize the distance "a" only poorly during an operation, the first mechanical exemplary embodiment of the alternative shown in FIG. 8 is to be preferred.

Figure 9:
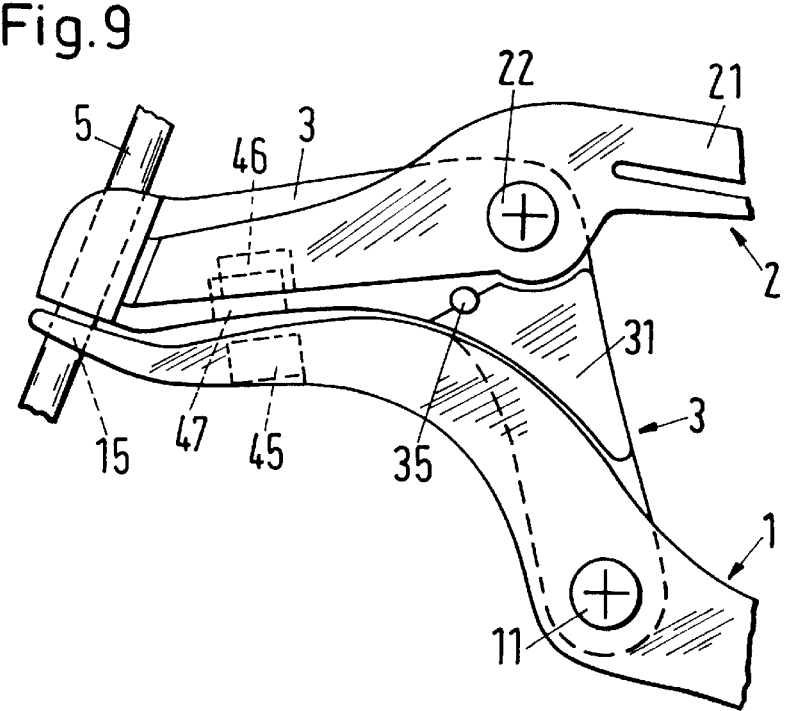
FIG. 9 shows a further alternative, in which magnet elements are substituted for the spring.

A further alternative is illustrated in FIG. 9 in which magnet elements 45, 46 and 47 which act on one another with magnetic attraction forces are substituted for the spring 4. At least one of these magnet elements is a permanent magnet 45; the other magnet element or elements 46 and 47 are ferromagnetic. The permanent magnet 45 or one of the permanent magnets is arranged in the first actuation lever 1 in the region between the insertion opening 15 and the lever joint 11; and the other magnet element or elements 46 and 47 are arranged at corresponding positions in the second actuation lever or in the third lever respectively.

What is claimed is:

1. A surgical instrument for tensioning a tension element, comprising a manually actuatable lever system with first and second actuation levers and a third lever connecting the first and second levers, the first lever having a laying-in opening and the second and third levers forming a clamping gap for receiving the tensioning element in the opening and the gap when the lever system is in a basic position, the third lever being asymmetrical, having only one side plate, and including a first clamping jaw component forming a U-shaped passage with a base surface defining a portion of the clamping gap, journalling bolts defining first and second lever joints, a single spring secured to the third lever, the spring having first and second limbs in contact with respective inner flanks of the first and second levers under a mechanical stress urging the flanks apart and the lever system into the basic position, the second lever having a second clamping jaw component which cooperates with the first clamping jaw component and extends into the U-shaped passage to define another portion of the clamping gap, a separately insertable abutment pin acting between the second and the third lever for preventing the spring from moving the lever system beyond the basic position, and a measuring device associated with one of the first and second levers for measuring a tensile force acting on the tension element.

2. A surgical instrument according to claim 1 wherein the measuring device comprises an elastically bendable beam and a reference beam, the beams being separated by a gap, joined at one end, and defining a portion of at least one of the actuation levers so that, upon applying a force to the at least one of the actuation levers, the beams deflect with respect to each other by an amount which is a function of a force applied to the at least one beam in opposition to the spring and urging the levers away from the basic position, and markings associated with the beams for communicating the degree to which the beams have moved relative to each other.

3. A surgical instrument according to claim 2 wherein the elastically bendable beam is arranged adjacent to the reference beam, wherein the beams extend substantially parallel to each other, and wherein the markings include segments arranged transversely to the beam direction and connected to the beams, the segments carrying indicators reflecting the relative deflection between the beams when the levers are moved away from the basic position.

4. A surgical instrument according to claim 3 wherein the beams include a bending restriction limiting the extent to which the beams can move relative to each other when the lever system is moved away from the basic position.

5. A surgical instrument according to claim 1 wherein at least one of the first and second actuation levers comprises a handle portion for gripping and a forward portion for engaging the tension element and applying a tension force to the tension element by moving the levers out of the basic position, a pivot joint connecting the portions, and a torque measuring device operatively coupled with the portions for measuring a torque acting on the portions about the pivot joint which is a function of the amount of tension applied to the tension element.

6. A surgical instrument according to claim 5 wherein the torque measuring device comprises one of a strain gauge and a piezoelectric crystal provided for determining the tension in the tension element, and including an electrical and/or electronic measurement arrangement operatively coupled with the one of the strain gauge and the piezoelectric crystal for indicating the tension in the tension element.

7. A surgical instrument according to claim 6 wherein the measurement arrangement is coupled to and the one of the strain gauge and the piezoelectric crystal is arranged on the at least one of first and second actuation levers.

8. A surgical instrument according to claim 1 wherein the measuring device comprises first and second beams forming part of the second lever, the beams having first ends coupled to each other and free second ends which define at least a portion of a gap, the beams being spaced apart and forming a free space between them, the beams being configured so that upon the application of a predetermined force to the second lever the beams elastically move toward and contact each other when a predetermined force has been applied to the second lever which urges the levers out of the basic position.

9. A surgical instrument according to claim 1 wherein the first actuation lever includes one of an eye and a gap between fork prongs defining the laying-in opening.

10. A surgical instrument according to claim 1 wherein the clamping gap is defined by jaws which have ribbings with ribbing edges on at least one surface defining the clamping gap, the ribbing edges extending transversely to a direction of tension in the tension member.

11. A surgical instrument in accordance with claim 1 wherein the measuring device includes an adjustable zero point display for determining the tension in the tension element.

* * * * *